(12) United States Patent
Ratna et al.

(10) Patent No.: US 8,019,555 B1
(45) Date of Patent: Sep. 13, 2011

(54) VIRUS AS A SCAFFOLD FOR HIERARCHICAL SELF-ASSEMBLY OF FUNCTIONAL NANOSCALE DEVICES

(75) Inventors: Banahalli Ratna, Woodbridge, VA (US); Amy Blum, Washington, DC (US); Carissa Soto, Alexandria, VA (US); Tina Brower, Alexandria, VA (US); Steve Pollack, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1617 days.

(21) Appl. No.: 10/911,767

(22) Filed: Jul. 30, 2004

(51) Int. Cl.
*C12Q 1/70* (2006.01)
*G01N 31/00* (2006.01)

(52) U.S. Cl. ............................ 702/22; 435/5

(58) Field of Classification Search .................. None
See application file for complete search history.

(56) References Cited

U.S. PATENT DOCUMENTS

| 6,430,511 | B1 | 8/2002 | Tour | |
|---|---|---|---|---|
| 6,459,095 | B1 | 10/2002 | Heath | |
| 6,500,611 | B2 | 12/2002 | Mattson | |
| 2003/0068900 | A1* | 4/2003 | Belcher et al. | 438/758 |

OTHER PUBLICATIONS

Price et al., Biphenyl- and Fluorenyl-based Potential Molecular Electronic Devices, Tetrahedron, 2003, 59, 3131-3156.*
Wang et al, Icosahedral Virus Particles as Addressable Nanoscale Building Blocks, Angew. Chem. Int. Ed. 2002, 41(3), 459-462.*
Taylor et al., Hindered fluorescence quenching in an insulated molecular wire, Org. Biomol. Chem., 2003, 1, 3851-3856.*
Lodha et al., Metal-molecule-semiconductor heterostructures for nano-device applications, IEEE, 2003, 311-314.*
Wu et al., Interaction of Fatty Acid Monolayers with Cobalt nanoparticles, nano letters, 2004, 4(2), 383-386.*
Tour et al., Molecular Scale Electronics: A synthetic/computational Approach to Digital Computing, j. Am. chem. Soc., 1998, 120, 8486-8493.*
Wang et al, "Icosahedral Virus Particles as Addressable Nanoscale Building Blocks", Angew. Chem. Int. Ed., vol. 41, No. 3, pp. 459-462, 2002.
Tour et al, "Molecular Scale Electronics: A Synthetic/Computational Approach to Digital Computing", J. Am. Chem. Soc., vol. 120, pp. 8486-8493, 1998.
Reed et al, "Molecular Random Access Memory Cell", American Institute of Physics, vol. 78, No. 23, pp. 3735-3737, 2001.
Reinerth et al, "Molecular Scale Electronics: Syntheses and Testing", Nanotechnology, vol. 9, pp. 246-250, 1998.
Price et al, "Biphenyl- and fluorenyl-Based Potential Molecular Electronic Devices", Tetrahedron, vol. 59, pp. 3131-3156, 2003.

* cited by examiner

*Primary Examiner* — Marjorie Moran
*Assistant Examiner* — Larry D Riggs, II
(74) *Attorney, Agent, or Firm* — Amy L. Ressing; Joseph T. Grunkemeyer

(57) ABSTRACT

An electrically active particle is disclosed, having a virus scaffold. Nanoparticles are bonded to the surface of the virus, and the nanoparticles are connected to each other by, molecular wires.

35 Claims, 9 Drawing Sheets

VIRUS AS A SCAFFOLD FOR HIERARCHICAL SELF-ASSEMBLY OF FUNCTIONAL NANOSCALE DEVICES

BACKGROUND OF THE INVENTION

1. Field of the Invention

The invention relates to an electrically active particle having a virus with bound nanoparticles and molecular wires.

2. Description of the Prior Art

Improvements in the speed and power of modern computers are produced mostly through increasing the number of available transistors in an integrated circuit. Although Moore's Law, which states that the number of transistors that can be fabricated on a silicon integrated circuit will double every 18 to 24 months, has been valid for the past 40 years, eventually the feature size of the transistors will small enough that quantum effects will prevent their operation. One possible alternative to traditional silicon-based technology is to use functional molecules as the building blocks of electronic devices. Instead of carving smaller and smaller patterns into silicon wafers, this bottom-up approach uses different types of molecules with functions such as wires, switches, and diodes, to build electronic circuits, and thus increasing the theoretical device density by up to 6 orders of magnitude.

Although a large number of molecules have been synthesized for their electronic properties, the problem remains in connecting these active molecules in such a way as to build logic circuits and functional electronic devices. Two of the approaches are (1) a crosswire device in which the electronically addressable molecules are sandwiched between the junction and (2) an array of containers with input and output pins on opposing sides with the molecules of interest bridging the two sets of pins.

SUMMARY OF THE INVENTION

The invention comprises a particle comprising a virus having a surface, a plurality of inorganic nanoparticles bound to the surface, and one or more molecular wires connecting the nanoparticles.

The invention further comprises a particle comprising a genetically engineered Cowpea Mosaic virus comprising cysteine residues on a surface of the virus, a plurality of gold nanoparticles bound to the cysteine residues, and one or more molecular wires selected from the group consisting of di-Pt, OPE, OPV, and OPV2 connecting the nanoparticles.

The invention further comprises a method of making a particle comprising the steps of: providing nanoparticles and a virus having a surface comprising virus binding groups capable of bonding to the nanoparticles; reacting the nanoparticles with the virus binding groups; providing a molecular wire; and reacting the molecular wire with the nanoparticles, thereby connecting the nanoparticles to each other.

BRIEF DESCRIPTION OF THE DRAWINGS

A more complete appreciation of the invention will be readily obtained by reference to the following Description of the Example Embodiments and the accompanying drawings.

DETAILED DESCRIPTION OF THE EXAMPLE EMBODIMENTS

Figure 1:
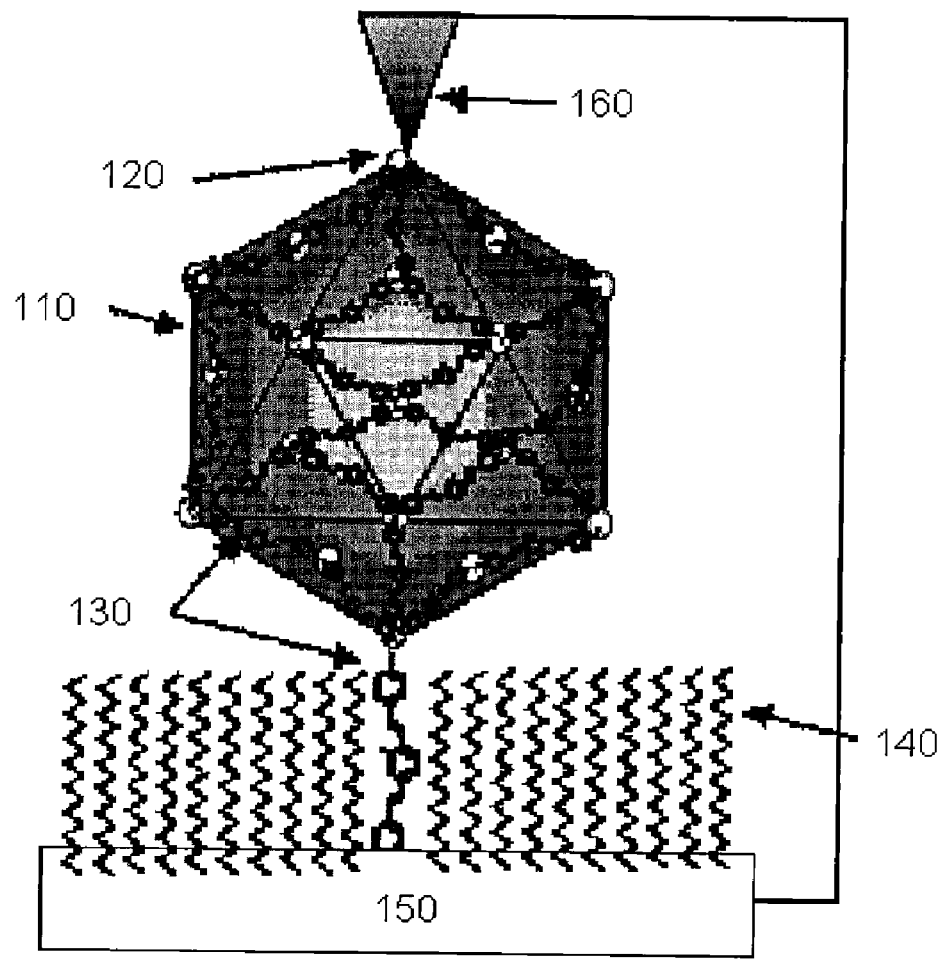
FIG. 1 schematically shows an assembly containing a particle of the invention.

The invention involves a way of interconnecting molecules of interest on the surface of a 30 nm virus particle. These modified particles can be self-assembled on a patterned electrode array, which provides the interface to the micro/macro device. One of the key issues in the field of molecular electronics is in designing a structure to connect the micron-scale contacts to the molecular-scale active components. The approach presented here represents a way to build circuits by organizing electronically active molecules on to a 30 nm virus structure that can itself be assembled onto larger electrodes to interface with current microchip technologies. Complex structures can be self-assembled using a solution-based approach without the need for expensive nanolithography. This approach provides a way to develop nanostructures in a massive scale at very low cost.

Viruses are simple acellular entities consisting of one or more molecules of DNA or RNA enclosed in a shell of protein. These proteins are polymers made of up to 20 different amino acids, which differ from each other in their side chains, linked together by peptide bonds. Because each protein has a specific sequence of amino acids, it has a well-defined structure. In a virus a well-defined number of these proteins assemble together to form the outer shell. The size of the assembled virus can vary from as small as 20 nm to as large as 400 nm. Using mutagenesis, it is possible to engineer specific amino acid residues to be placed at desired locations on this protein coat with specified distances between them. Because of the specificity associated with the proteins, the virus particles can be a scaffold to attach different entities, thus creating patterns of functionalities.

The virus has the ability to bond to nanoparticles. This property may be found in a naturally occurring virus or a genetically engineered virus. One way to have the binding ability is for the virus to have cysteine or histidine residues on its surface. Cysteine is readily capable of bonding to metallic nanoparticles due to its thiol moiety. Histidine also has some capability of bonding to metal nanoparticles. These residues may already be present on the surface of some viruses, or they may be engineered into the virus. The surface of the virus may also have linking molecules that can bond to the particles. Such linking molecules would be added to an already complete virus.

Virus shells are frequently are made of several copies of the same protein. This allows for the bonding sites on the surface to be in a repeating pattern. Different patterns of bonding sites may be made be genetically engineering cysteine into the virus surface at different locations. The proteins on the viruses can be crosslinked to make them more stable.

Suitable viruses include, but are not limited to, icosahedral viruses, cylindrical viruses, non-phage viruses, and viruses lacking a lipid encapsulation. An example of a suitable virus is Cowpea Mosaic Virus (CPMV), a plant virus whose structure is established and for which mutants are available. The CPMV capsid protein is an icosahedron with a diameter of 30 nm, formed by 60 identical copies of an asymmetric subunit. The virus particles are stable to a wide variety of conditions, including temperatures up to 60° C., the presence of a number of organic solvents, and pH values from 3.5 to 9 indefinitely at room temperature, making them suitable for further reaction under many different conditions. In its natural state, the CPMV virus contains no cysteine amino acids on the exterior capsid surface. Thus, there are no naturally occurring thiol groups on the virus surface.

Engineered cysteine mutants of CPMV can provide a scaffold for attachment of gold nanoparticles to the available thiol group. Engineering can be achieved using methods such as those disclosed in Johnson et al., *Annu. Rev. Phytopathol.*, 1997, 35, 67; and Wang et al., *Angew. Chem. Int. Ed.*, 2002, 41, 459, both incorporated herein by reference. Specific binding of 2 and 5 nm gold particles with different patterns of specific interparticle distances in three dimensions has been demonstrated. Because the virus consists of 60 identical subunits, a single added cysteine will produce 60 reactive thiols, while adding two cysteines will produce 120 reactive thiols. The introduced cysteines at the capsid surface can generate sulfur-gold covalent bonds, which are much stronger than any non-covalent, non-specific electrostatic interactions that may occur between the gold particle and the virus. Because each viral capsid is chemically and geometrically identical, the gold nanoparticles bind at specific locations on the virus to produce well-defined patterns. The pattern of arrangement of Au nanoparticles on the unstained virus observed by Transmission Electron Microscopy (TEM) not only confirms the specific binding of the Au nanoparticles to the SH groups on the cysteines, but also shows the absence of non-specific binding on the surface.

By a careful selection of the position of the inserted cysteine residue and the size of the gold nanoparticles, the gaps between the adjacent gold nanoparticles can be tuned in the 2-3 nm range such that a dithiolated molecule bridge across them using sulfur-gold bonds. Such an interconnection of the Au nanoparticles can generate a 3-dimensional network of conducting molecules.

The nanoparticles are capable of bonding to the binding sites on the surface of the virus. Suitable nanoparticle materials include, but are not limited to, metal, gold, palladium, platinum, nickel, zinc, silver, transition metals, coinage metals, semiconductors, CdSe, PdSe, PdS, II-VI semiconductors, IV-VI semiconductors, metal oxide, $TiO_2$, and ZnO. When the nanoparticle is metal, it may be bonded to the surface of the virus by metal-sulfur covalent bonds, such as when the bonding site is cysteine.

The nanoparticles are bonded to the virus according to a method determined by the chemical composition of each. The reaction may be spontaneous, as in metal nanoparticles bonding to cysteine groups. Other combinations may require certain reaction conditions, which are known in the chemical art.

The nanoparticles may comprise an organic coating such as long chain fatty acid, oleic acid, and trioctylphosphine/trioctylphosphine oxide (TOP/TOPO). The coating can control the growth of the nanoparticles and prevent aggregation. Molecules of the coating may be displaced when the nanoparticles bond to the virus and the molecular wire. Alternatively the coating may be entirely removed, such as by reaction with a thiol compound.

The molecular wire is a molecule that is bonded to two or more nanoparticles. Such molecules can contain conjugated moieties terminated by binding groups capable of binding to the nanoparticles. The conjugated groups may be unsaturated organic groups and/or organometallic groups, including, but not limited to, aromatic, heteroaromatic, alkene, alkyne, transition metal complex, and transition metal complex having one or more stabilizing ligands, such as triphenylphosphine and tributylphosphine. Suitable binding groups include, but are not limited to, sulfur-containing group, isocyanide, pyridyl, S-acetyl, selenium, tellurium, and group VI elements. The binding group may be bound directly to a conjugated moiety, or there may be an intervening methylene group. Eq. (1)-(4) show examples of suitable molecular wires. There can also be a combination of different molecular wires present in a single particle, both between nanoparticles and between a nanoparticle and a substrate as described below. The names and molecular lengths of these are compounds are di-Pt, 30.1 Å; oligophenylene ethynylene (OPE), 20.2 Å; thioacetic acid S-[4-(2-{4-[2-(4-acetylsulfanylmethyl-phenyl)-vinyl]-2,5-dibutoxy-phenyl}-vinyl)-benzyl] ester (oligophenylene vinylene, OPV), 20.7 Å; and OPV2, 18.2 Å.

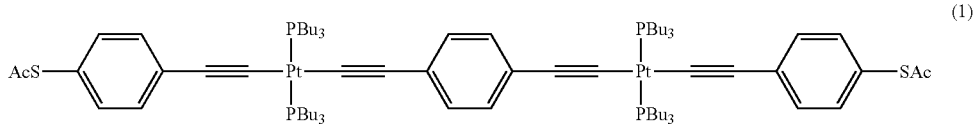

(1)

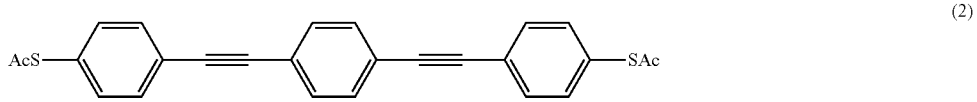

(2)

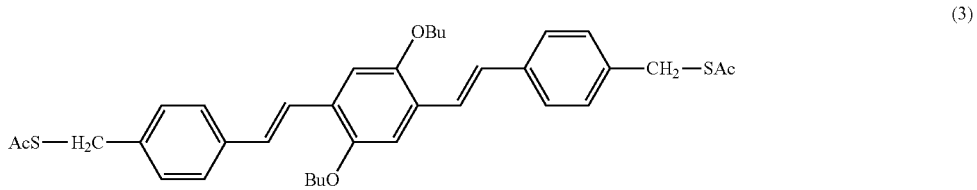

(3)

-continued

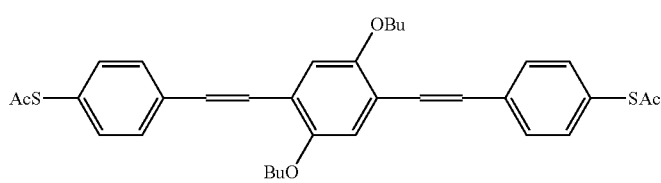

(4)

The molecular wire may also spontaneously bond to the nanoparticles, or may require certain reaction conditions. The molecular wire may contain a protecting group before it is reacted with the nanoparticles, to prevent polymerization of the molecular wires. The examples in Eqs. (1)-(4) contain an acetyl protecting group on each sulfur atom to prevent thiol polymerization. The acetyl group can be removed by a de-protecting compound, such as acid or base, after the molecular wire is mixed with the nanoparticle-containing virus. The resulting $S^-$ groups then bond to the nanoparticles. Another example protecting group is trimethylsilylethyl, which can be removed with fluoride. Eq. (5) shows an example molecular wire, (2-{[4-((E)-2-{2,5-dibutoxy-4-[(E)-2-(4-{[2-(trimethylsilyl)ethyl]sulfanyl}phenyl)ethenyl]phenyl}ethenyl)phenyl]sulfanyl}ethyl)(trimethyl) silane, with this protecting group.

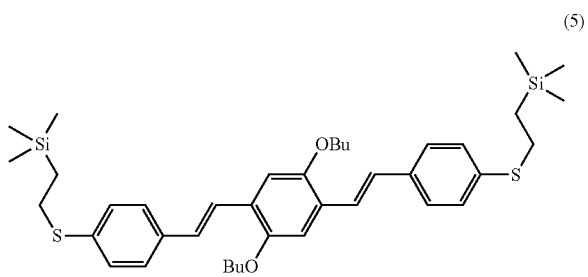

(5)

High efficiency heterobond forming reactions with minor or no side products can be used for the final bonding between the conductive nodes and an active "core." Specifically, 4-azidothiolphenylacetate can be adsorbed onto metal surfaces. Then the 1,3 dipolar addition of the azido group with a terminal alkyne on the molecular wire yields a conjugated 4-thiophenyl-6-aryl-1,2,3-triazole linkage.

The molecules used for connecting the nanoparticles can have a wide variety of properties including, conduction, switching, and diode like behavior. These molecules can be donor-acceptor or push-pull molecules, photoelectric and rectifying molecules and from a larger set of macromolecules capable of logic function.

The particle can be used as part of an assembly with a metal or highly doped substrate. An additional molecular wire, which may be the same as or different from those connecting the nanoparticles to each other, connects a nanoparticle to the substrate, thus tethering the particle to the substrate. There is also an insulator molecule on the substrate to insulate the rest of the substrate from the particle. The insulator may cover part of all of the substrate, except for the location where the molecular wire is bonded. A suitable insulator is, but is not limited to, an alkane.

The assembly may be used as part of a sensor. The particle may be conductive, and this conductivity may be altered in the presence an analyte, when electrostatic interactions between the analyte and the molecular wire changes the energy levels of the orbitals in the wire. This presence of this change in conductivity may be determined when the particle is contacted with a sample suspected of containing the analyte.

Having described the invention, the following examples are given to illustrate specific applications of the invention. These specific examples are not intended to limit the scope of the invention described in this application.

The following is a general procedure for binding 5 nm gold nanoparticles to a virus. Aggregated virus is removed from the stock by running stock virus solution through a desalting column. 23.68 mL of 5 nm gold particles (used as received) is mixed with 1.184 mL of 1 M $KPO_4$ buffer at pH 5.9 and 35.6 μg of virus in a sealed tube. The mixture is incubated for 3 days at room temperature to allow binding to occur. After 3 days, the total volume is concentrated to approximately 100 μL. 10 μL of 20 mM thioctic acid is added to the concentrated virus-nanoparticle solution. The mixture is incubated for 15 minutes in an Eppendorf tube at room temperature to coat the gold nanoparticles in thioctic acid. After 15 minutes, 5 μL of 10× TBE buffer and 5 μL of glycerol are added to prepare the same for gel electrophoresis. A gel is prepared from a solution 1% low melting agarose. The virus-gold nanoparticle mixed is loaded into the gel, and the gel is run in 10×TBE buffer at 103 V for approximately 45 minutes to separate the virus with attached gold nanoparticles from unreacted free gold nanoparticles. To recover the virus with attached gold nanoparticles, the upper red band is cut from the gel with a gel cutter. The gel pieces are placed in 10× TAE buffer in an electric field until the virus+gold complexes have migrated out of the gel and into solution.

The following is a general procedure for binding a molecular wire to the nanoparticles. A virus/nanoparticle stock solution of $\sim 4.313 \times 10^{-6}$ mole/L in THF is prepared. This solution is left in the freezer until time of use. A stock solution of di-Pt of approximately the same molarity is prepared and stored in the freezer. A 50/50 solution of OPV2 stock and di-PtSH stock is prepared. Add 750 μL virus solution to 150 μL of OPV2/di-PtSH stock solution for a 80:20 by volume virus to molecule solution. The solution is left for at least 6 hours but no more than 12 hours. It is then washed twice with a 2× more by volume 80:20 $KPO_4$ buffer and THF solution and then twice with $KPO_4$ buffer. The resultant VNB is then measured by UV and fluorescence. The filtrate is saved and also measured to confirm that the VNB was rid of free molecule.

Example 1

Figure 2A:
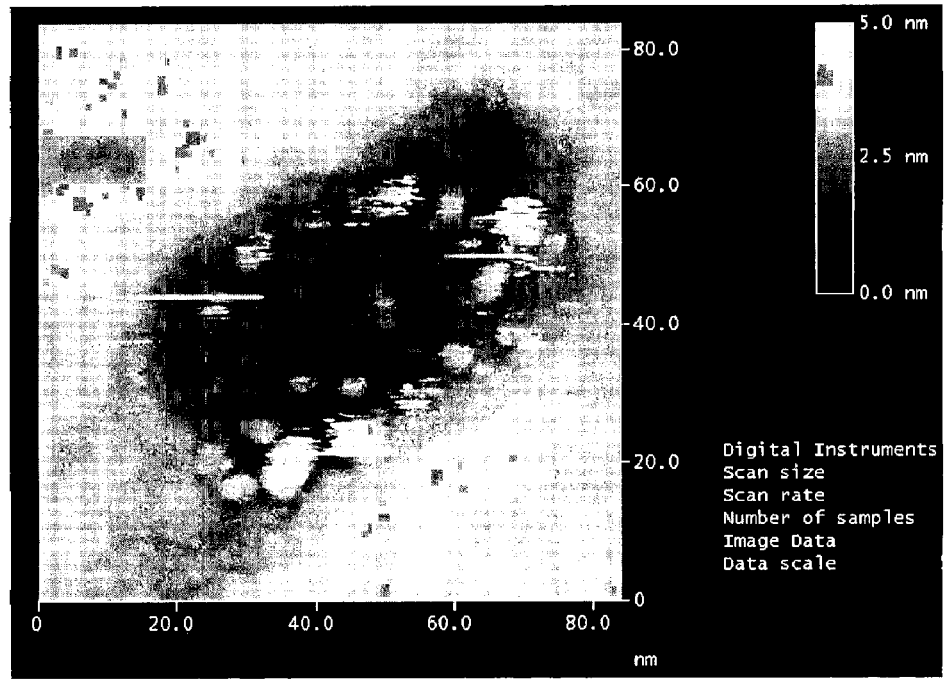
FIGS. 2(a) and 2(b) show STM images of a particle, with (2(b)) and without (2(a)) a network across the virus.
Figure 2B:
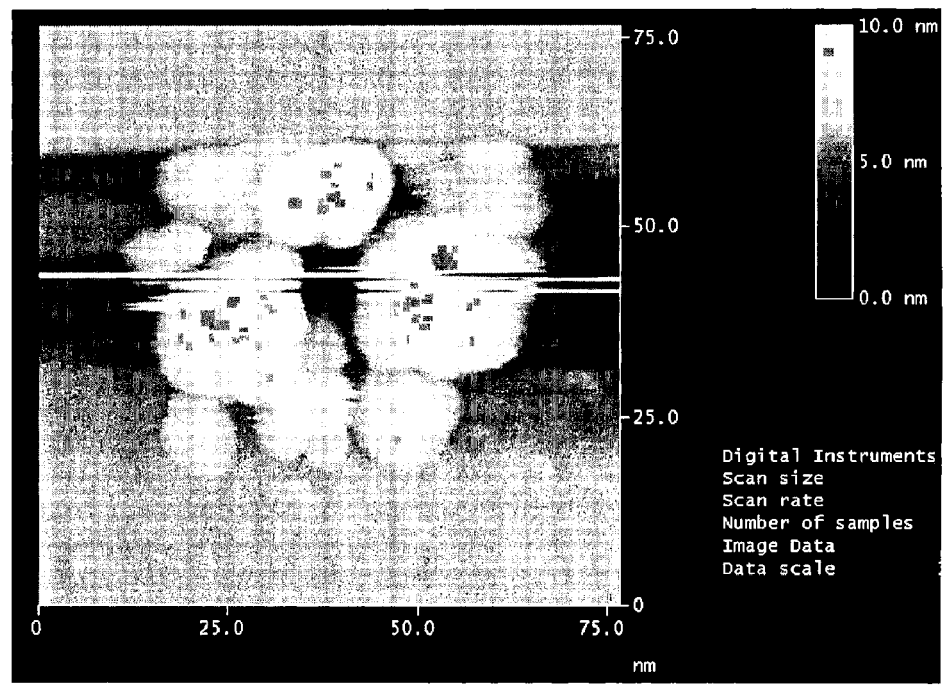
Figure 3:
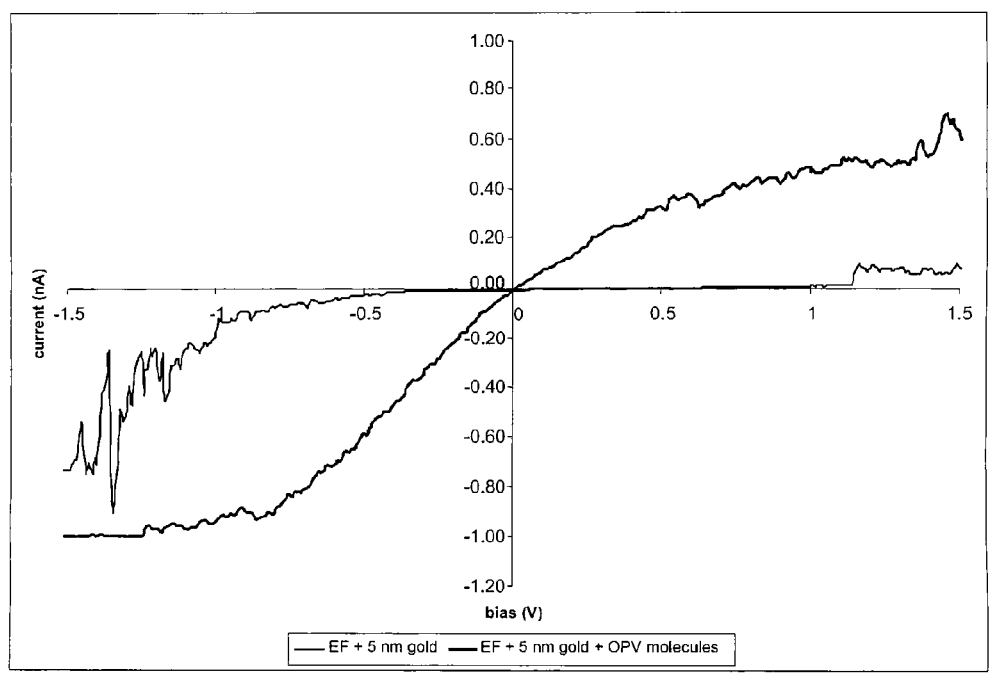
FIG. 3 shows the difference in the conductivity between the virus particles without and with the molecules attached.

Au nanoparticles on CPMV—One network that has been created using a cysteine mutant decorated with 5 nm Au particles that were connected using two different dithiolated molecules forming the network. The structures of the molecules used for forming this network are di-Pt (Eq. (1)) and OPV (Eq. (3)). I-V characteristics of these molecules have been well studied (Blum et al., *Appl. Phys. Lett.*, 2003, 82, 3322; Kushmerick et al., *J. Am. Chem. Soc.*, 2002, 124, 10654; Kushmerick et al., *Ann. IVY Acad. Sci.*, 2003, 1006, 277, all incorporated herein by reference). The attachment of the molecules to the Au nanoparticles on the virus nanoblock (VNB) was confirmed by looking at the fluorescence of the OPV molecules. The conductivity of this network across the virus span was measured using STM 160 by attaching the VNB 110 with gold nanoparticles 120 to a conducting molecule 130 inserted in a monothiol-$C_{11}$ monolayer 140 on Au coated mica 150, as shown in FIG. 1. (The STM images shown in FIGS. 2(*a*) and 2(*b*) are for this system, with (2(*b*)) and without (2(*a*)) the molecular wires.) FIG. 3 shows the difference in the conductivity between the virus particles without and with the molecules attached.

Figure 4:
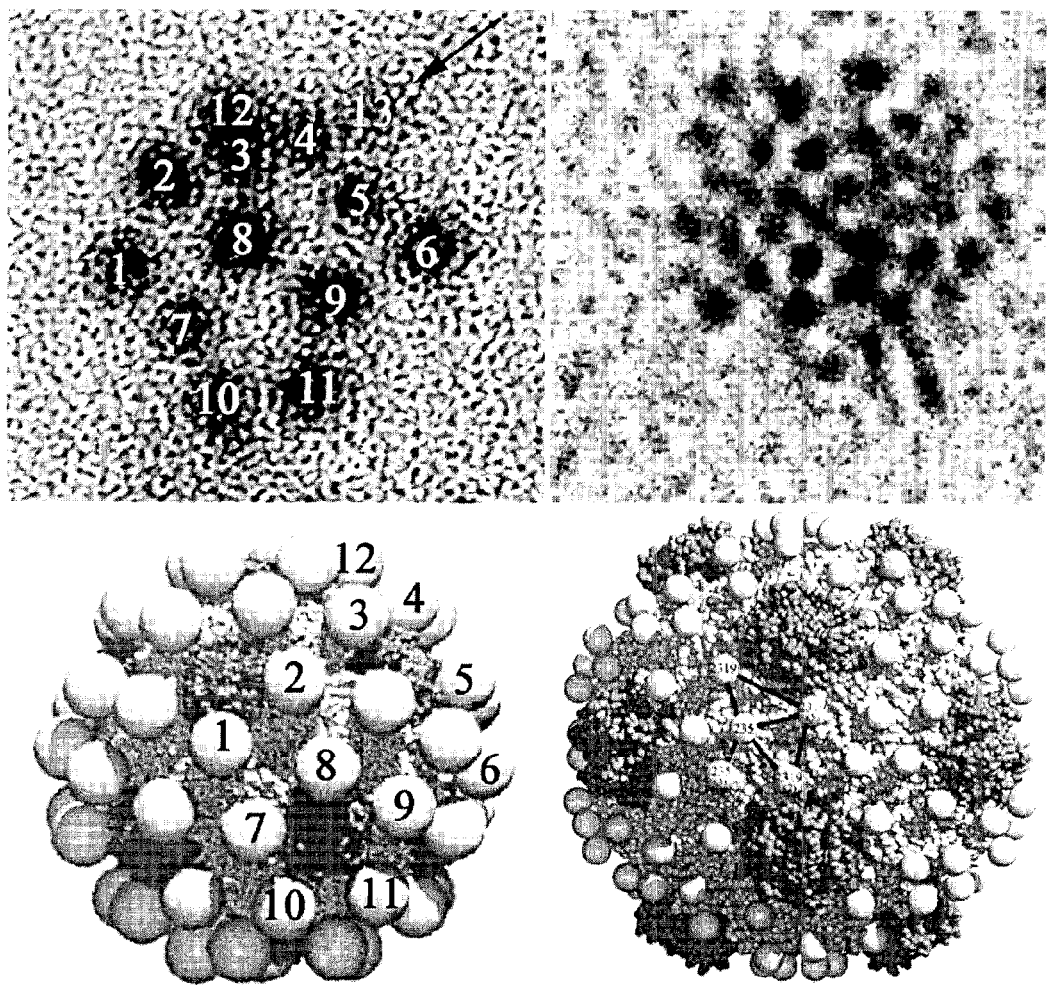
FIG. 4 shows the patterns generated by 5 and 2 nm gold particles on two different CPMV mutants.

FIG. 4 shows the patterns generated by 5 and 2 nm gold particles on two different mutants. Once the nanoparticles are bound to the virus, the 2 to 3 nm distance between the gold nanoparticles can be bridged with electronically active molecules, using the same thiol-gold chemistry used to make the initial gold patterns. Before putting the molecules on the VNB, the virus acts as an insulator. After the molecules are put on, current can flow through the network built on the virus. FIG. 2 shows scanning tunneling microscopy (STM) data on the virus before and after putting the molecules on. STM images represent a convolution of topographic and electronic information. Thus, on the top image, the viruses are less conductive than the film they are isolated in, so they appear dark, even though they are 30 nm taller than the background film. After adding molecules to the virus, shown on the bottom, the virus appears brighter than the surrounding film, because now current can flow through the conductive network on the viral scaffold.

Example 2

Figure 5:
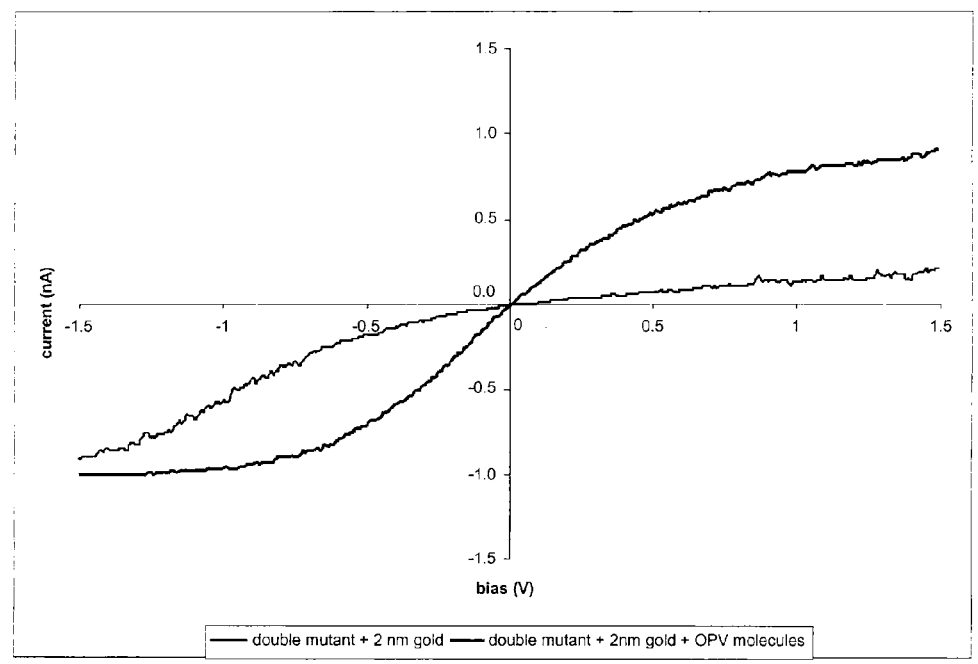
FIG. 5 shows the difference in the conductivity between the double mutant virus particles without and with the molecules attached.

Double mutant CPMV—Similar experiments described in Example 1 were carried out for a different set of the virus and molecules. In this case, a conductive network has been created on a double mutant to which 2 nm gold particles have been attached. The neighboring Au particles were interconnected using only OPV2 molecules (Eq. (4)). The difference in the conductance between the two conductive VNBs is clear in the I-V plots of FIG. 5; showing again the difference in conductance between the virus particles before and after attachment of molecules. The conductance of the network on this virus is distinctly different and higher than the conductance of the single mutant virus discussed in Example 1.

Example 3

Figure 6:
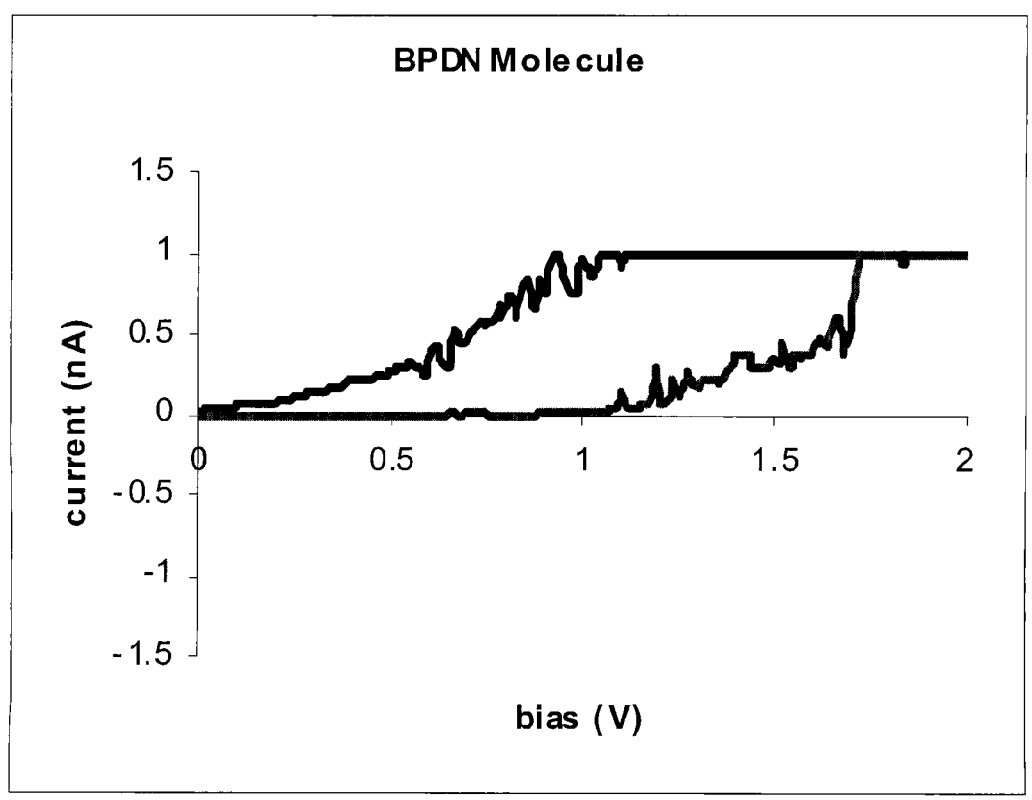
FIG. 6 shows I-V curves for BDPN.

Molecular wire with two conducting states—The above two examples describe the process used to generate a three-dimensional network of conducting molecules. Another conducting molecule whose molecular structure is shown in Eq. (6) exhibits two conducting states depending on the I-V sweep history. For example, depending on the scan direction, the molecule at 1V can be either be almost nonconducting (FIG. 6, lower curve) or conducting 1 nA.

Example 4

Figure 7:
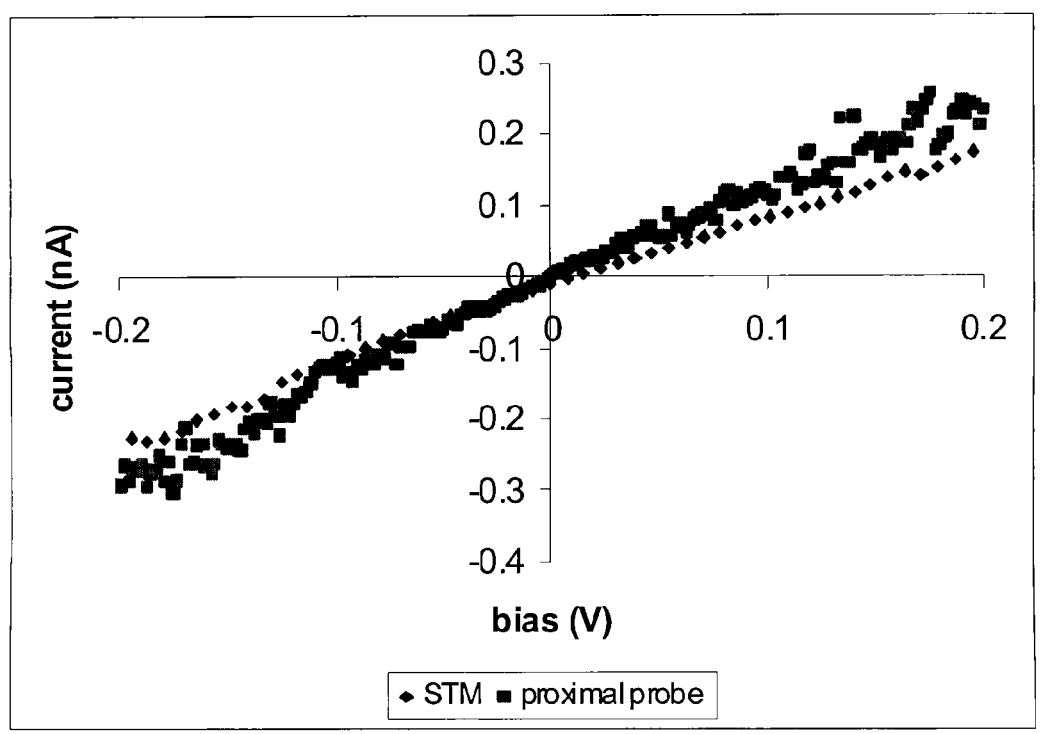
FIG. 7 shows a proximal probe conductance measurement as compared to an STM measurement.

Proximal probe measurement—The conductance of the particle was also measured by placing a cluster of the CPMV particles on a substrate in a gap between two gold leads. The leads were 100 nm wide, with a 30 nm gap between the leads. FIG. 7 shows a proximal probe conductance measurement as compared to an STM measurement.

Example 5

Figure 8A:
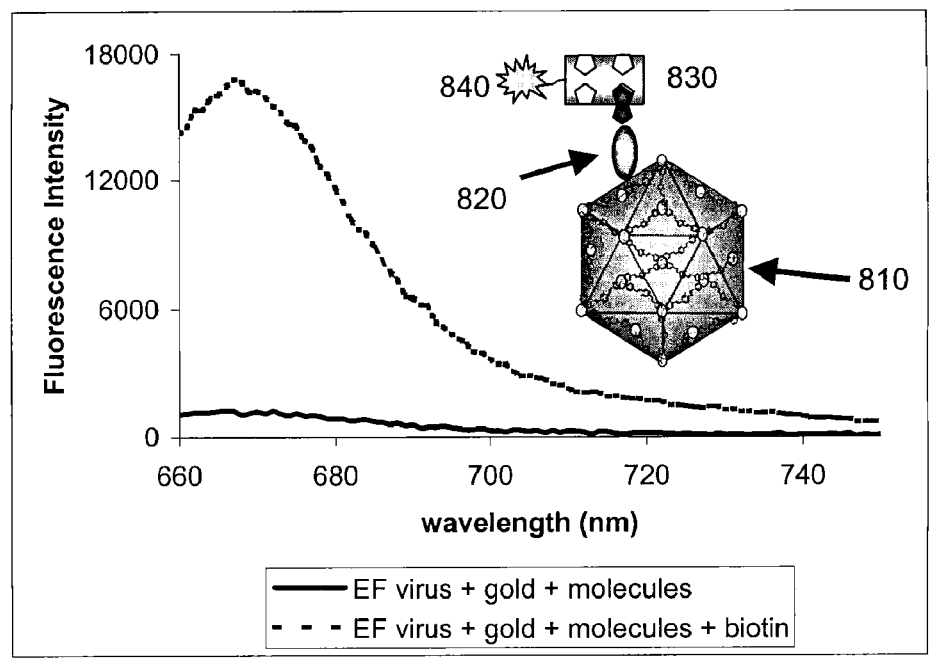
FIG. 8(a) shows fluorescence data demonstrating that biotin put on the lysines of a conductive VNB is still active.
Figure 8B:
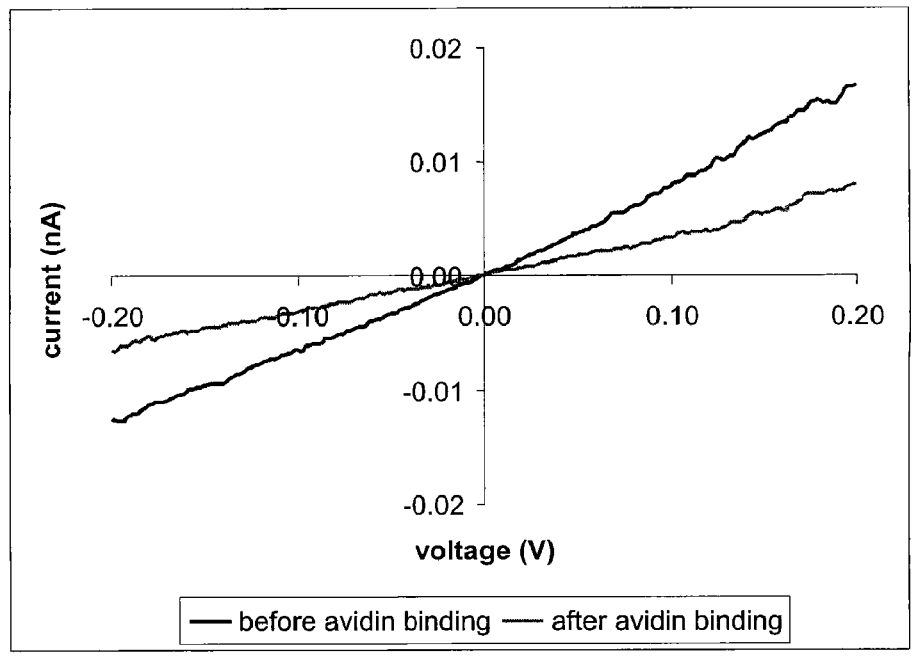
FIG. 8(b) shows sensor conductance before and after exposure to virus.

Sensor—The configuration from Example 4 was used a sensor for avidin. FIG. 8(*a*) schematically shows the conductive VNB 810, with bound NHS-LC biotin 820, avidin 830, and fluorescing cy5dye 840, and fluorescence data demonstrating that biotin put on the lysines of a conductive VNB is still active, since it binds cy5-labeled avidin FIG. 8(*b*) shows conductance in the proximal probe before and after exposing the virus to non-labeled avidin.

Example 6

Figure 9:
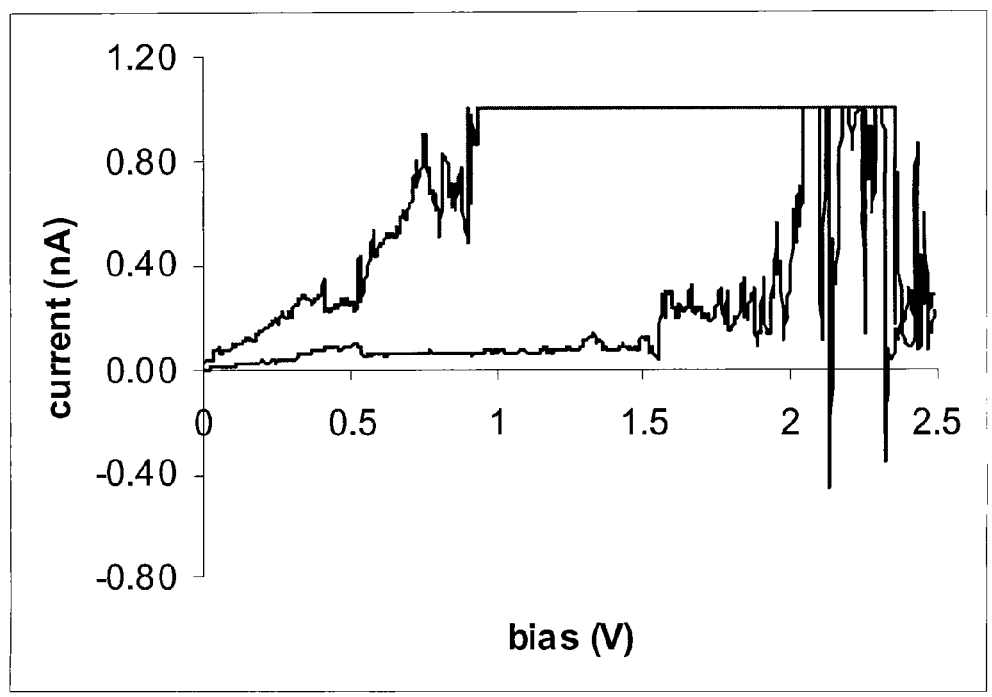
FIG. 9 shows multiple conductive states for a memory bit.

Memory bit—The molecule shown in Eq. (6) was used as the molecular wire. By replacing some or all of the molecules on the virus network by the BPDN molecules, the network can be made to switch between two conducting states. This virus then would act as a memory bit. The molecule had two conductive states, when placed in the proximal probe. FIG. 9 shows multiple conductive states. When a voltage greater than about 1.5 V was applied to the particle, the resistance of the network was lowered, such that a current of at least 1 nA (the limit of the measuring instrument) was produced when 1 V was later applied. When about 0 V was applied, the resistance increased, such that very little current was produced when 1 V was later applied.

Obviously, many modifications and variations of the present invention are possible in light of the above teachings. It is therefore to be understood that the claimed invention may be practiced otherwise than as specifically described.

What is claimed is:

1. A particle comprising:
   a virus having a surface;
   a plurality of inorganic nanoparticles bound to the surface; and
   one or more molecular wires connecting the nanoparticles.

2. The particle of claim 1, wherein the virus is a naturally occurring virus.

3. The particle of claim 1, wherein the virus is a genetically engineered virus.

4. The particle of claim 1, wherein the virus is selected from the group consisting of icosahedral viruses, cylindrical viruses, non-phage viruses, and viruses lacking a lipid encapsulation.

(6)

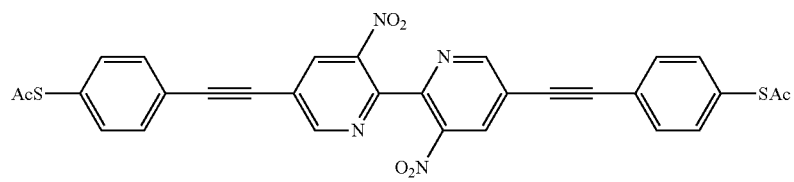

5. The particle of claim 1, wherein the virus is a genetically engineered Cowpea Mosaic virus comprising cysteine residues on the surface.

6. The particle of claim 1, wherein the surface comprises cysteine residues.

7. The particle of claim 1, wherein the surface comprises histidine residues.

8. The particle of claim 1, wherein the surface comprises linking molecules capable of bonding to the nanoparticles.

9. The particle of claim 1, wherein the nanoparticles are bonded to the surface in a repeating pattern.

10. The particle of claim 1, wherein the nanoparticles are metal nanoparticles.

11. The particle of claim 10, wherein the metal nanoparticles comprise gold.

12. The particle of claim 10, wherein the metal nanoparticles comprise a metal selected from the group consisting of palladium, platinum, nickel, zinc, silver, transition metals, and coinage metals.

13. The particle of claim 10, wherein the metal nanoparticles are bound to the surface by metal-sulfur covalent bonds.

14. The particle of claim 1, wherein the nanoparticles comprise a material selected from the group consisting of semiconductors, CdSe, PdSe, PdS, II-VI semiconductors, IV-VI semiconductors, metal oxide, $TiO_2$, and ZnO.

15. The particle of claim 1, wherein the molecular wire comprises conjugated moieties terminated by binding groups capable of bonding to the nanoparticles.

16. The particle of claim 15, wherein the molecular wire comprises one or more unsaturated organic conjugated moieties.

17. The particle of claim 15, wherein the molecular wire comprises one or more conjugated organometallic moieties.

18. The particle of claim 15, wherein the conjugated moieties are independently selected from the group consisting of aromatic, hetero aromatic, alkene, alkyne, transition metal complex, and transition metal complex having one or more stabilizing ligands.

19. The particle of claim 18, wherein the stabilizing ligands are independently selected from the group consisting of triphenylphosphine and tributylphosphine.

20. The particle of claim 15, wherein the binding group is a sulfur-containing group.

21. The particle of claim 15, wherein the binding group comprises a group selected from the group consisting of isocyanide, pyridyl, S-acetyl, selenium, tellurium, and group VI elements.

22. The particle of claim 15, wherein the binding group is bound directly to one of the conjugated moieties.

23. The particle of claim 15, wherein the binding group is bound to a methyl group, and the methyl group is bound to one of the conjugated moieties.

24. The particle of claim 1, wherein the molecular wire is selected from the group consisting of di-Pt, OPE, oligophenylene ethylene vinylenes, OPV, and OPV2.

25. An assembly comprising:
the particle of claim 1;
a metal or highly doped semiconductor substrate;
an insulator molecule on the substrate; and
a second molecular wire connecting the substrate and one of the nanoparticles.

26. The assembly of claim 25, wherein the insulator molecule is an alkane.

27. The particle of claim 1, wherein the nanoparticle comprises an organic coating.

28. The particle of claim 27, wherein the coating is selected from the group consisting of long chain fatty acid, oleic acid, and trioctylphosphine/trioctylphosphine oxide.

29. A particle comprising:
a genetically engineered Cowpea Mosaic virus comprising cysteine residues on a surface of the virus;
a plurality of gold nanoparticles bound to the cysteine residues; and
one or more molecular wires selected from the group consisting of di-Pt, OPE, OPV, and OPV2 connecting the nanoparticles.

30. A method of making a particle comprising the steps of:
providing nanoparticles;
providing a virus having a surface comprising functional groups capable of bonding to the nanoparticles;
reacting the nanoparticles with the functional groups;
providing a molecular wire; and
reacting the molecular wire with the nanoparticles, thereby connecting the nanoparticles to each other.

31. The method of claim 30, wherein the step of providing a virus comprises genetically engineering the virus to have cysteine residues on the surface.

32. The method of claim 30, further comprising the steps of:
providing a metal or highly-doped semiconductor substrate having an insulator molecule; and
reacting the particle and the substrate with an additional molecular wire, thereby connecting a bound nanoparticle to the substrate.

33. The method of claim 30, wherein the, molecular wire comprises a protecting group, and further comprising the following step before the step of reacting the molecular wire with the nanoparticles:
reacting the molecular wire with a de-protecting compound.

34. The method of claim 33,
wherein the protecting group is selected from the group consisting of acetyl and trimethylsilylethyl; and
wherein the de-protecting compound is selected from the group consisting of acid, base, and fluoride.

35. The method of claim 30, further comprising the step of:
contacting the particle with a sample suspected of containing an analyte that changes the conductivity of the particle.

* * * * *